United States Patent
Pepin et al.

(10) Patent No.: US 10,299,723 B2
(45) Date of Patent: May 28, 2019

(54) ULTRA-LOW POWER ONE-SHOT HYDRATION SENSING SYSTEM

(71) Applicant: Verily Life Sciences LLC, Mountain View, CA (US)

(72) Inventors: Brian Pepin, Oakland, CA (US); Robert Wiser, San Francisco, CA (US)

(73) Assignee: Verily Life Sciences LLC, Moutain View, CA (US)

( * ) Notice: Subject to any disclaimer, the term of this patent is extended or adjusted under 35 U.S.C. 154(b) by 0 days.

(21) Appl. No.: 15/614,680

(22) Filed: Jun. 6, 2017

(65) Prior Publication Data

US 2017/0354374 A1    Dec. 14, 2017

Related U.S. Application Data

(60) Provisional application No. 62/349,314, filed on Jun. 13, 2016.

(51) Int. Cl.
| | |
|---|---|
| *G08B 21/20* | (2006.01) |
| *A61B 5/00* | (2006.01) |
| *A61F 13/42* | (2006.01) |
| *G08B 25/10* | (2006.01) |

(Continued)

(52) U.S. Cl.
CPC .......... *A61B 5/6808* (2013.01); *A61B 5/0002* (2013.01); *A61B 5/4261* (2013.01); *A61B 5/7445* (2013.01); *A61F 13/42* (2013.01); *G08B 21/20* (2013.01); *G08B 25/10* (2013.01); *A61B 5/0022* (2013.01); *A61B 5/01* (2013.01); *A61B 5/486* (2013.01); *A61B 5/4875* (2013.01); *A61B 2562/029* (2013.01); *A61B 2562/0271* (2013.01); *A61F 2013/424* (2013.01); *G01F 1/68* (2013.01)

(58) Field of Classification Search
None
See application file for complete search history.

(56) References Cited

U.S. PATENT DOCUMENTS

| | | | |
|---|---|---|---|
| 4,796,014 A | | 1/1989 | Chia |
| 6,200,250 B1 * | | 3/2001 | Janszen .................. A61F 13/42 493/334 |

(Continued)

OTHER PUBLICATIONS

Fox Van Allen, "Smart Diaper Tech Sends Wireless Wetness Alerts", Techlicious, Feb. 10, 2014.

(Continued)

*Primary Examiner* — John F Mortell
(74) *Attorney, Agent, or Firm* — McDonnell Boehnen Hulbert & Berghoff LLP

(57) ABSTRACT

A moisture-sensitive device is provided that includes a dissolvable conductive material. Exposure of the dissolvable conductive material to urine or some other fluid causes the dissolvable conductive material to dissolve, increasing an effective resistance of the dissolvable conductive material. This change in resistance can be detected to determine the presence of an aqueous fluid. In response to such detection, a transmitter can then provide a wireless transmission indicative of the presence of the fluid. This moisture-sensitive device can be provided in a diaper and transmissions produced by the device can be detected using a smart phone or other device and used to indicate to a user that the diaper has been soiled.

18 Claims, 9 Drawing Sheets

(51) Int. Cl.
   *A61B 5/01*    (2006.01)
   *G01F 1/68*    (2006.01)

(56) References Cited

U.S. PATENT DOCUMENTS

| | | | | |
|---|---|---|---|---|
| 6,490,515 | B1* | 12/2002 | Okamura | B60N 2/002 |
| | | | | 180/273 |
| 8,071,888 | B2* | 12/2011 | Shiraishi | C09D 11/52 |
| | | | | 174/257 |
| 2004/0147888 | A1 | 7/2004 | Huang et al. | |
| 2008/0300559 | A1* | 12/2008 | Gustafson | A61F 13/42 |
| | | | | 604/361 |
| 2009/0315728 | A1* | 12/2009 | Ales, III | A61F 13/42 |
| | | | | 340/604 |
| 2010/0182023 | A1* | 7/2010 | Pena | G01N 17/04 |
| | | | | 324/700 |
| 2011/0095884 | A1 | 4/2011 | Xu et al. | |
| 2013/0160608 | A1* | 6/2013 | Nusko | B22F 1/0025 |
| | | | | 75/370 |
| 2016/0125759 | A1* | 5/2016 | Dougherty | G09B 19/00 |
| | | | | 434/236 |
| 2016/0170776 | A1* | 6/2016 | Bergstrom | A61F 13/42 |
| | | | | 713/100 |
| 2016/0328584 | A1* | 11/2016 | Rokhsaz | H01Q 5/335 |

OTHER PUBLICATIONS

"Japan sensor will let diaper say baby needs changing", http://phys.org/news/2014-02-japan-sensor-diaper-baby.html, Feb. 10, 2014.

Douseki et al., "Self-powered Wireless Disposable Sensor for Welfare Application", 35th Annual International Conference of the IEEE EMBS, Osaka, Japan, Jul. 3-7, 2013, pp. 1664-1667.

* cited by examiner

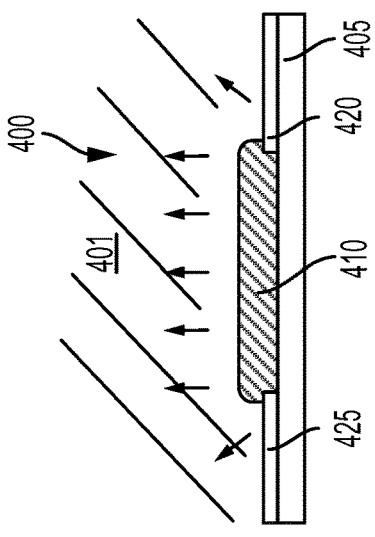
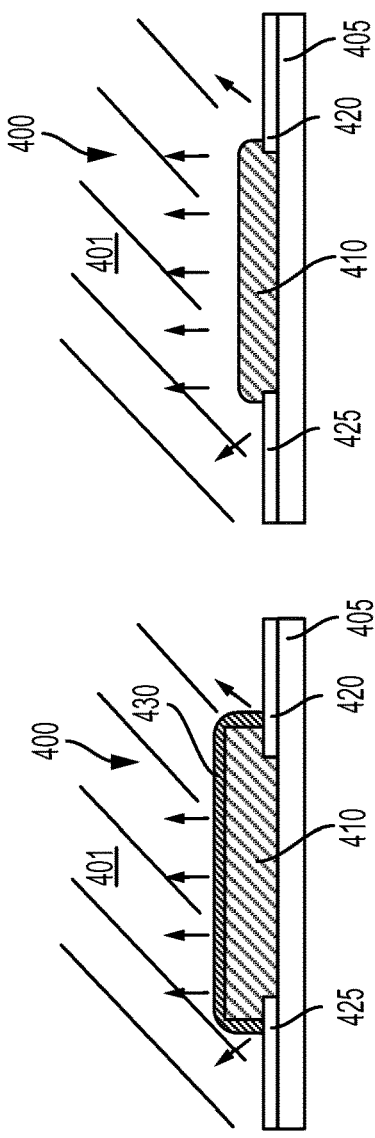
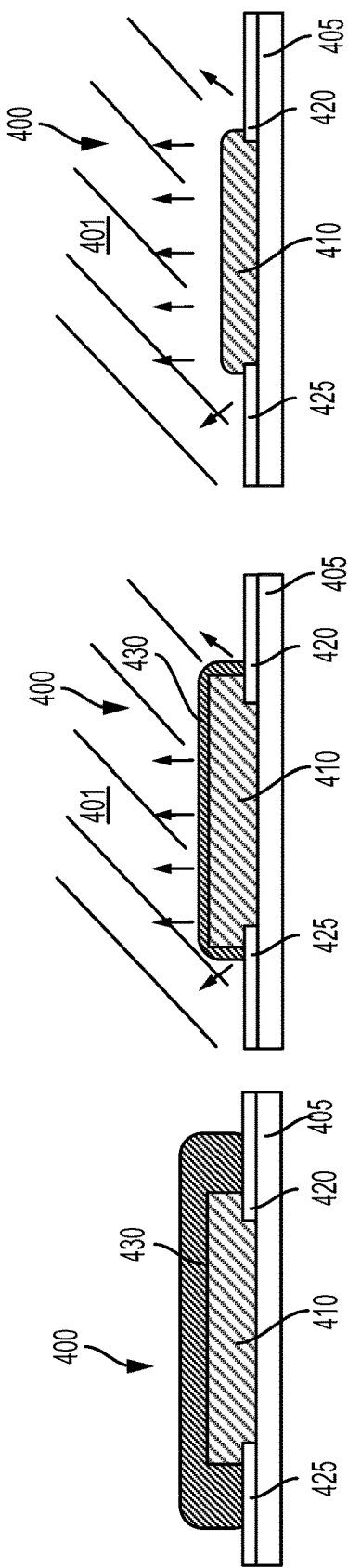
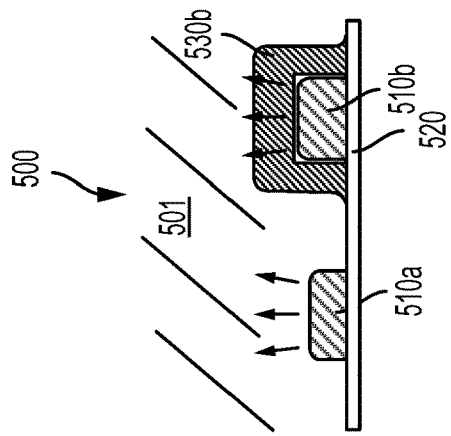
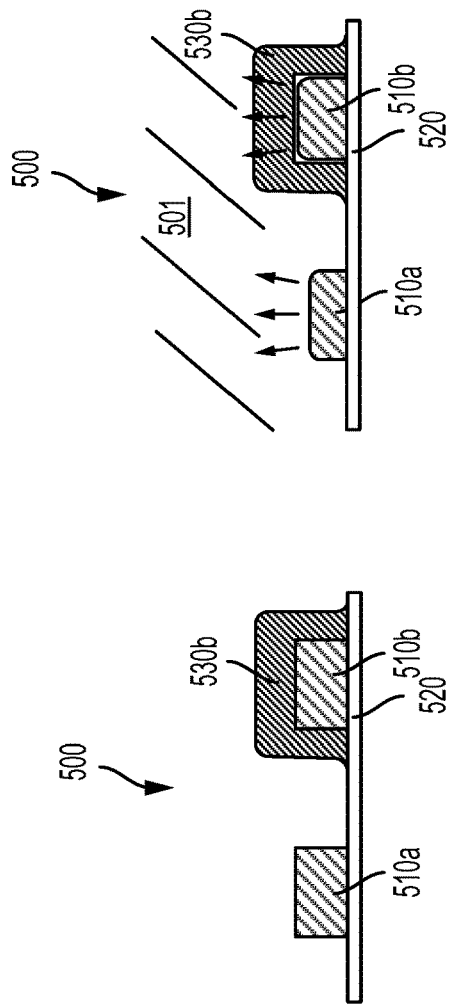

ULTRA-LOW POWER ONE-SHOT HYDRATION SENSING SYSTEM

CROSS-REFERENCE TO RELATED APPLICATIONS

This application claims the benefit of and incorporates by reference the content of U.S. Provisional Pat. App. No. 62/349,314, filed Jun. 13, 2016.

BACKGROUND

Unless otherwise indicated herein, the materials described in this section are not prior art to the claims in this application and are not admitted to be prior art by inclusion in this section.

Prompt changing of a soiled diaper can improve health outcomes, e.g., by reducing a chance of infection, by reducing skin irritation, or by some other mechanisms. Such diapers may be worn by infants or by adults. A variety of sensors are available to detect the presence of moisture and/or to otherwise detect that a diaper has been soiled, e.g., by detecting a fluid, a humidity, a temperature, a local conductivity, the presence or concentration of a chemical within and/or in the environment of the diaper, or by some other means.

SUMMARY

Some embodiments of the present disclosure provide a system including: (i) a transmitter; (ii) a moisture sensor that includes a dissolvable conductive material that dissolves in an aqueous fluid; and (iii) a controller operably coupled to the transmitter and the moisture sensor. The controller (1) operates the moisture sensor to detect the presence of the aqueous fluid proximate the system; and (2) operates the transmitter to transmit a radio-frequency signal in response to detecting the presence of the aqueous fluid proximate the system.

Some embodiments of the present disclosure provide a method including: (i) detecting an aqueous fluid using a moisture sensor, wherein the moisture sensor includes a dissolvable conductive material that dissolves in the aqueous fluid; and (ii) responsive to detecting the aqueous fluid, operating a transmitter to transmit a radio-frequency signal.

Some embodiments of the present disclosure provide a method of forming a moisture-sensitive system including: (i) depositing a precursor solution on a substrate, wherein conductive traces are disposed on the substrate, and wherein depositing a precursor material on the substrate includes depositing the precursor material such that the deposited precursor material is in contact with at least one of the conductive traces; and (ii) curing the precursor solution to form a dissolvable conductive material that dissolves in an aqueous fluid.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4A is a cross-sectional view of a moisture sensor.

FIG. 4B is a cross-sectional view of the moisture sensor of FIG. 4A after a portion of the moisture sensor has dissolved.

FIG. 4C is a cross-sectional view of the moisture sensor of FIG. 4B after a portion of the moisture sensor has dissolved.

FIG. 5A is a cross-sectional view of a moisture sensor.

FIG. 5B is a cross-sectional view of the moisture sensor of FIG. 5A after portions of the moisture sensor have dissolved.

DETAILED DESCRIPTION

Figure 1:
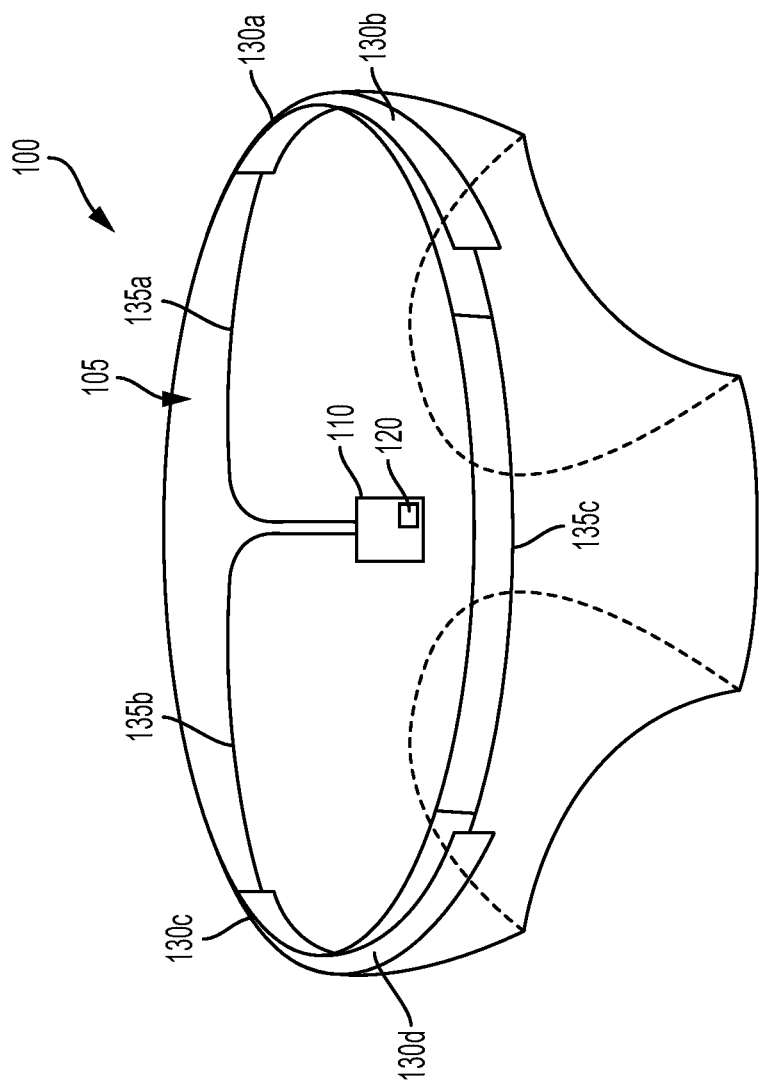
FIG. 1 is a perspective view of a moisture-sensitive device disposed in a diaper.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

It can be beneficial in a variety of applications to detect the presence of moisture and/or fluids in an environment. For example, the presence of moisture in sensitive equipment, in the basement of a house, or some other environment of interest could be detected and used to take some preventive action, e.g., deactivating electronics or equipment, activating a sump pump, closing a valve that is providing the fluid, or taking some other action. In another example, the presence of urine, feces, or other sources of moisture in a diaper could be detected and such detection could be indicated to a person (e.g., a caretaker) such that the caretaker could change the diaper. By detecting moisture in a diaper (or other environment of interest) soon after the moisture is introduced, responsive actions (e.g., changing a diaper) may be performed more effectively or in a manner that otherwise improves outcomes (e.g., by reducing skin irritation and/or reducing a risk of infection or other sequelae of protracted exposure to urine and/or feces).

Devices and systems may be configured in a variety of ways to facilitate moisture detection. Such devices may be configured to be stored for a protracted period of time before use, to be fabricated at low cost, or according to some other considerations. In response to detecting moisture, such devices could generate a wireless transmission to alert some other systems or devices to the presence of the detected moisture, e.g., to a smartphone that could provide an auditory, visual, or other indication to a user to inform the user that moisture is present (e.g., such that the user could then change a diaper in which the moisture was detected). Such a wireless transmission could be generated according to a Bluetooth Low Energy communication protocol or according to some other communications standards.

A moisture-sensitive device as described herein could include a variety of different means for detecting the presence of moisture. In some examples, such a device could include an electrochemical cell that produces a voltage in response to exposure to a fluid (e.g., in response to the fluid acting as a solvent for the cell, providing a medium for chemical exchange between electrodes of the cell, and/or some other mechanism). Additionally or alternatively, such a device could include an element of a conductive material that dissolves in the presence of moisture such that the presence of moisture could be detected by detecting a change in the effective resistance of the element of dissolvable conductive material as the element dissolves. A moisture-sensitive device could include other means for detecting moisture and/or fluids or could include multiple means for moisture detection.

A moisture-sensitive device as described herein could be configured to operate in a low-power mode such that the device can operate for a protracted period of time to detect moisture, to provide wireless transmissions or other indications that moisture has been detected, or to perform such other operations and/or to be stored for a protracted period of time before being operated in such a way. Such a low-power mode could include a controller of the device being maintained in a reset state. Additionally or alternatively, a battery or other power source of the device could be disconnected from other elements of the device until the device is to be used. This could include joining conductive clasps of a diaper together to couple the battery to a controller, transmitter, or other elements of the device. Un-joining such clasps could act to deactivate the device, e.g., to cause the device to cease generating wireless transmissions. Such a device could additionally or alternatively be powered by a fluid-sensitive battery that is stored in a dry state, such that the battery may be stored for a protracted period of time until providing power to the device upon exposure to moisture.

One or more of a fluid-sensitive battery, a moisture sensor, a transmitter, an antenna, a user output, electronics, or other components of such a moisture-sensitive device could be flexible; for example, the fluid-sensitive battery could include a thin, flexible layers of metal, metal oxide, woven conductive material, fluid-absorbent separator material, or other elements. In some examples, such a device, or one or more elements of such a device, could be incorporated into a diaper such that the flexible portions of the device that are incorporated into the diaper minimally interfere with motion of a wearer of the diaper. Further, elements of such a device could be disposed using low-cost methods onto a flexible substrate of the device and/or onto a fabric element or other part of a diaper. For example, metallic traces and/or electrodes (e.g., to interconnect elements of the device, to provide electrodes of a battery) could be formed by photo-patterning or other methods on a flexible substrate. In another example, inkjet printing, screen printing, or other methods could be used to dispose materials on a flexible substrate (e.g., to provide a precursor material to form a dissolvable, conductive material if a moisture sensor).

It should be understood that the above embodiments, and other embodiments described herein, are provided for explanatory purposes, and are not intended to be limiting. While embodiments of moisture-sensitive devices are described herein as being incorporated into diapers and configured to detect the presence of urine and/or feces in such diapers, other embodiments are anticipated that are configured to be mounted to and/or disposed within different environments. For example, a moisture-sensitive device configured to detect the presence of moisture and to provide wireless transmission response to such detection could be configured to detect the presence of moisture in a basement, beneath a sink, tub or basin, on or near a pipe or other element of plumbing, on or within an electronic device, or in some other environment of interest.

II. Example Moisture Sensor

As noted above, a moisture sensor can be incorporated into a variety of devices (e.g., diapers, flexible adhesive patches) to facilitate moisture detection in a variety of environments (e.g., within a diaper, on or near plumbing, within the enclosure of electronics). Such devices could be configured to facilitate such detection over a protracted period of time and/or to be stored for a protracted period of time before being operated to detect moisture. This could include operating such devices to generate wireless transmission only after moisture has been detected. Further, such devices could be configured to be manufactured cheaply (e.g., by including screen- or inkjet-printed components) such that the devices and/or elements thereof could be incorporated into disposable items, e.g., disposable diapers.

A moisture-sensitive device and/or elements of a moisture sensor of such a device could be incorporated into a diaper and could operate to detect the presence of urine or feces in the diaper. Such diapers could be wearable by infants or by adults. Such devices could, in response to detecting the presence of moisture, transmit an alert or generate some other wireless transmission. Such a transmission could be received by a smartphone, a server, a hospital wireless network, or some other system(s) configured to indicate that the diaper should be changed or to perform some other operations (e.g., to log the timing or other information about the detected moisture) in response to receiving such a wireless transmission. For example, a parent's smartphone could receive such a wireless transmission and indicate to the parent that a child's diaper needs to be changed. In another example, a computer, display, indicator light, or other system at a nurse's station could provide an indication, in response to receiving such a wireless transmission, that a patient's diaper needs to be changed.

FIG. 1 is a perspective view of an example diaper 100 that includes a moisture-detecting device 110. The diaper could be sized to be worn by an infant, by a child, by an adult, or by some other person or animal. It is noted that relative dimensions in FIG. 1 are not necessarily to scale, but have been rendered for purposes of explanation only in describing the arrangement of a moisture-detecting device and/or a diaper in which such a device is incorporated. The moisture-detecting device 110 includes a moisture-sensitive element 120 that can be operated to detect the presence of moisture in the diaper 100. Note that the illustrated location of the moisture-detecting device 110 within the diaper 100 is intended as a non-limiting example and that the moisture-detecting device 110 may be located at other locations on or within the diaper 100 to facilitate detection of moisture. In an example, the moisture-detecting device 110 may be located at the front of the diaper such that the moisture-sensitive element 120 is disposed at a location to facilitate detection of urine produced by a wearer of the diaper 100. Further, the diaper 100 and/or moisture-detecting device 110 may be configured to facilitate detection of moisture, e.g., by including absorbent materials, moisture barriers, or other elements configured to direct moisture to the moisture-sensitive element 120, to transport moisture away from the skin of a wearer of the diaper 100, to maintain moisture proximate the moisture-sensitive element 120, or to facilitate some other processes.

Further, one or more elements of such a device could be configured to be removably attached to the diaper to facilitate reuse. For example, a battery, a controller, a transmitter, one or more buttons or other user interface elements, circuitry, or other components of a device could be disposed in a reusable module. Such a module could be configured to mount onto a diaper (e.g., via magnets, adhesive, a clip, Velcro, pins, and/or some other means) such that the module is in electrical contact with one or more fluid-sensitive batteries, moisture sensors, other moisture-sensitive elements, and/or some other sensors or elements incorporated into the diaper (e.g., a flex-sensitive element disposed around the diaper to facilitate detection of breathing). Such a module could include pins, conductive pads, or other means for making electrical contact with conductive thread, conductive dyes, or other conductive elements incorporated in the diaper, e.g., to provide an electrical connection between a mounting location of the module to the diaper (e.g., a location near a waistband of the diaper) and a location of other or more moisture sensors or other elements incorporated into the diaper (e.g., a location of a fluid-sensitive battery at the front of the diaper to facilitate detection of urine). Following detection of urine by such a device, the module could be removed from the diaper and mounted to another diaper to facilitate detection or urine or feces in the new diaper.

The diaper 100 also includes clasps 130a, 130b, 130c, 130d that can be connected to each other to secure the diaper 100 onto a wearer. Such clasps could be wholly or partially conductive (e.g., by incorporating a flexible conductive material and/or including a woven conductive material) to facilitate some applications. For example, such conductive clasps could be used to determine whether the diaper 100 is being worn by a wearer and/or to determine that the diaper 100 has been removed. This could include coupling two or more of the clasps 130a, 130b, 130c, 130d to the moisture-detecting device 110 (e.g., to a controller of the moisture-detecting device 110 via the flexible conductors 135a, 135b, 135c shown in FIG. 1) such that the clasps 130a, 130b, 130c, 130d being connected to each other can be detected or otherwise used to control some aspect of the operation of the moisture-detecting device 110. This could include using the conductive clasps to couple a battery of the moisture-sensitive device 110 to a controller or other elements of the moisture-detecting device 110 (e.g., such that the device 110 ceases transmitting when the clasps are disconnected and/or such that a battery of the device 110 is not discharged until the diaper 100 is being worn).

The moisture-detecting device 110 may be flexible, e.g., to improve comfort of the diaper 100 or to provide for some other considerations. For example, a moisture-sensitive device could be flexible and could include an adhesive such that the device could be adhered to a variety of different objects having a variety of different shapes, e.g., to a curved portion of plumbing. The moisture-detecting device 110 being flexible could include elements of the moisture-detecting device 110 being disposed on a flexible substrate and/or the elements of the device being, themselves, flexible. In such examples, a patch antenna, a loop antenna, a dipole antenna, a ground plane, a fractal antenna, or some other type of antenna could be formed from metallic traces disposed on a surface of such a flexible substrate and/or the device 110 could include a chip antenna or some other configuration of antenna for generating radiative wireless signals. A battery may be provided to power the device 110 (e.g., to power a controller or other components to use the moisture-sensitive element 120 to detect the presence of moisture and/or to operate a transmitter to generate wireless transmissions). Such a battery could, itself, be used as the moisture-sensitive element 120, e.g., the battery could be a fluid-sensitive battery that is configured to produce an electrical voltage when exposed to moisture (e.g., when exposed to urine). Such a battery could be flexible.

The moisture-detecting device 110 could include a variety of electronic components. For example, the moisture-detecting device 110 could include a controller, amplifiers, analog-to digital converters, comparators, voltage converters, temperature sensors, transmitters, radios, transceivers, chip antennas, rectifiers, or some other component or components. Such components can be mounted to and/or electrically connected via interconnects or traces patterned on a printed circuit board or other substrate (e.g., a flexible substrate). Further, antennas, electrodes, capacitors, resistors, or other components could be formed from such traces or other interconnects formed on the surface of a substrate. A loop, dipole, coil, fractal, or other type of antenna can be one or more layers of conductive material patterned on a surface of a substrate of the device 110 to form one or more specified conductive shapes (e.g., a ring, a spiral, a curved or straight line, an elliptical or rectangular patch, a fractal). Electrical interconnects (e.g., traces), antennas, and/or conductive electrodes (e.g., for a switch, moisture sensor, for a battery, for a fluid-sensitive battery, for interfacing with conductive clasps, etc.) can be formed from conductive materials patterned on the substrate by a process for precisely patterning such materials, such as deposition, lithography, etc. The conductive materials patterned on the substrate can be, for example, gold, platinum, palladium, titanium, carbon, aluminum, copper, silver, silver-chloride, conductors formed from noble materials, metals, combinations of these, etc.

The moisture-detecting device 110 could be configured to operate in a low-power mode (e.g., a sleep mode) and to, in response to receiving and/or detecting one or more of a variety of activation events, transition into a high-power mode (e.g., a mode wherein wireless transmissions or other indications are generated). Such activation events can include the detection, using the moisture-sensitive element 120, of moisture (e.g., detecting the presence of urine in the diaper 100). Additionally or alternatively, the moisture-detecting device 110 could be configured to operate in a low- or no-power state by being disconnected from a power source (e.g., a battery) until the device is activated by connecting the power source. In some examples, this could include connecting the conductive clasps 130a, 130b, 130c, 130d together (e.g., to secure the diaper 100 to the body of a wearer). Conversely, the moisture-detecting device 110 could be deactivated (e.g., could be caused to cease generating wireless transmissions and/or to enter a low- or no-power state) by disconnecting the clasps 130a, 130b, 130c, 130d. The controller or other electronics of the moisture-detecting device 110 could be coupled to a battery via the clasps; alternatively, the connection and/or disconnection of the clasps could be detected (e.g., by a comparator, a logic gate, and/or a pull-up resistor) and used to control some aspect of the operation of the moisture-detecting device 110.

The moisture-detecting device 110 could be configured to perform multiple different functions (e.g., to detect multiple different properties of a wearer) in a number of different ways. For example, the moisture-detecting device 110 could include a first battery to provide power for electronics of the moisture-detecting device 110 and a fluid-sensitive battery to detect moisture and/or to provide additional power. The moisture-detecting device 110 could include a moisture sensor that includes an element of dissolvable conductive material, a fluid-sensitive battery, and/or some other moisture-sensitive components. Further, such a device could include multiple instances of a particular moisture-sensitive component, e.g., multiple fluid-sensitive batteries. Such multiple moisture-sensitive components could differ in some way such that some additional information could be determined using the multiple components. This could include locating such multiple moisture-sensitive components at respective different locations to detect the spatial distribution of moisture in an environment of interest (e.g., within a diaper). Additionally or alternatively, each moisture-sensitive component could differ with respect to one or more properties (e.g., a sensitivity to moisture, a time-dependence of dissolution of a dissolvable conductive element, a sensitivity to one or more ions or other contents of moisture) to facilitate detection of some additional information about detected moisture (e.g., to facilitate detection of an amount of the moisture, an osmolarity of the moisture, a concentration of one or more ions or other analytes in the moisture).

In an example, each fluid-sensitive battery of a set of such batteries could include a respective different battery chemistry, electrolyte chemistry, electrode configuration, analyte-permeable coating or encapsulation, or other properties such that each fluid-sensitive battery responds differently to the presence or concentration of a respective different analyte in a sample of detected moisture. In another example, a number of moisture sensors, each including a respective element of dissolvable conductive material, could differ with respect to a size and/or composition of the element of dissolvable material. Such multiple moisture sensors could be configured to facilitate the detection of an amount of moisture, a composition of the moisture, to control a sensitivity or other property of one or more of the moisture sensors to moisture (e.g., a relationship between an amount of moisture and an effective resistance of a circuit comprising one or more of the moisture sensors), or to facilitate some other functionality of the moisture-detecting device 110.

The moisture-detecting device 110 could include additional components according to an application. For example, the moisture-detecting device 110 could include temperature-sensitive elements, chemical sensors, gas sensors, accelerometers, or other sensors. Such sensors could be used to detect properties of detected moisture (e.g., a concentration or ions or other analytes in urine received by the moisture-detecting device 110), of the body of a wearer of the diaper 100 (e.g., a body temperature), of activities of a wearer of the diaper 100 (e.g., by operating an accelerometer), an ambient light level, or some other properties of interest. Such detected properties could be wirelessly transmitted to some other system (e.g., to a smartphone, a server in a clinician's office, or some other system) to be used to determine some information, e.g., about the health of a wearer of the diaper 100. Additionally or alternatively, such detected properties could be used to control some aspects of the operation of the moisture-detecting device 110, e.g., to begin or cease transmitting wireless signals, to begin or cease detecting moisture using the moisture-sensitive element(s) 120, or to perform some other operations and/or change an operational mode.

The moisture-sensitive element 120 could include a variety of components configured to facilitate the detection of moisture. Such detection could include detecting the presence of moisture, an amount of moisture that is present, or detecting some other properties of moisture to which the moisture-sensitive element 120 is exposed. In some examples, the moisture-sensitive element 120 could include a fluid-sensitive battery. A fluid-sensitive battery includes an electrochemical cell that is configured to provide an electrical voltage (e.g., between first and second electrodes of the fluid-sensitive battery) when the fluid-sensitive battery is exposed to an aqueous (or other) fluid (e.g., urine). Being exposed to the aqueous fluid could provide a conductive path between electrodes of the battery, could dissolve a salt or other electrolyte of the battery, or cause the fluid-sensitive battery to provide a voltage via some other mechanism(s).

A fluid-sensitive battery as described herein could be configured in a variety of ways. In some examples, one or more components of the fluid-sensitive battery could be absorbent, to facilitate the battery providing a voltage in response to exposure to a fluid. For example, a separator, electrode, or other components of the fluid-sensitive battery could be composed of fabrics, felts, expanded polymers, or other absorbent materials. Such materials could be composed of hydrophilic materials, have specified weave or pore dimensions or geometries, or be otherwise configured to facilitate absorption of an aqueous fluid such that the fluid-sensitive battery provides a voltage. Further, one or more electrodes of the fluid-sensitive battery could include an absorbent conductive material to increase an effective surface area of the electrode(s) (e.g., to increase a current and/or power capacity of the battery).

Figure 2A:
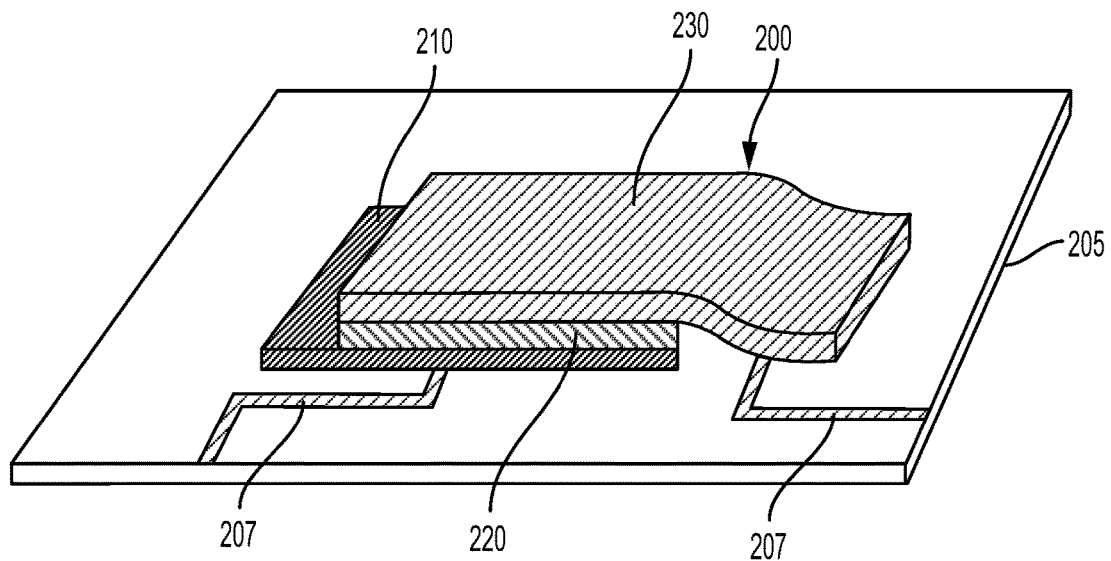
FIG. 2A is a perspective view of a fluid-sensitive battery.
Figure 2B:
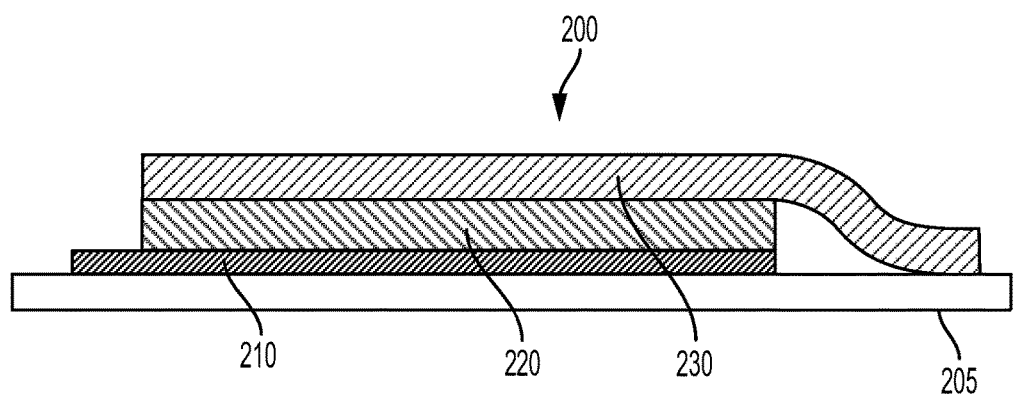
FIG. 2B is a cross-sectional view of the fluid-sensitive battery of FIG. 2A.

FIGS. 2A and 2B illustrate perspective and cross-sectional views, respectively, of an example fluid-sensitive battery 200 disposed on a substrate 205. The fluid-sensitive battery includes a first electrode 210 and a second electrode 230 that are both in contact with, and separated by, a separator 220. The first 210 and second 230 electrodes are electrically coupled to traces 207 formed on the substrate 205. The separator 220 and second electrode 230 are composed of absorbent materials such that the separator 220 and second electrode 230 can absorb an aqueous fluid. The first electrode 210 may also be composed of absorbent materials. The composition of the first electrode 210, separator 220, second electrode 230, and any electrolyte materials that may be disposed within one or more of the first electrode 210, separator 220, second electrode 230 may be specified according to a variety of different chemistries such that, when the battery 200 is exposed to an aqueous fluid, a voltage is provided between the first electrode 210 and the second electrode 230.

The separator 220 may be composed of a variety of different absorbent materials. Such materials may be selected and/or formed to prevent direct, non-ionic electrical conduction between the first 210 and second 230 (or further) electrodes of the battery 200. For example, the separator 220 could be composed of paper, a non-conductive fabric, a felt, an absorbent polymer material, or some other non-conductive absorbent material.

The first 210 and/or second 230 electrodes could be composed of absorbent and/or porous materials to facilitate absorption of a fluid of interest and/or to increase an effective surface area of the electrode(s) (e.g., to increase a current and/or power capacity of the battery 200 when exposed to an aqueous fluid). In particular, the second electrode 230 may be composed of an absorbent conductive material to allow an aqueous fluid to travel through the second electrode 230 and be absorbed by the separator 220. Such absorbent materials could include woven or otherwise aggregated strands of a conductive material, e.g., woven metal wires or strips, woven carbon fibers, woven conductive polymer fibers, a felt composed of short carbon fibers, or some other woven materials. Additionally or alternatively, the material of one or both of the electrodes 210, 230 could be modified or processed to increase its surface area, e.g., by roughening. Further, activated carbon or some other particulate conductive substance could be added to one or both of the electrodes 210, 230 to increase the surface area of the interface between the conductive material of the electrode(s) and aqueous fluid absorbed by the battery 200.

An electrolyte of the battery 200 could be present in an aqueous fluid to which the battery 200 is exposed (e.g., sodium, potassium, chloride, or other ions present in urine). Additionally or alternatively, components of such an electrolyte could be provided on or within the elements of the battery 200. For example, sodium chloride or some other salt(s) could be present, in the form of dry crystals or some other dry state, within the absorbent material of one or more of the separator 220 or the second electrode 230. Such electrolyte materials may be disposed within the absorbent materials of the battery 200 by exposing the element(s) of the battery 200 to a solution containing the electrolyte and subsequently drying the element(s) of the battery. This process could occur before, during, or after the element(s) are assembled into the battery 200. The particular chemical composition of the electrolyte could be selected according to the chemistry of the first 210 and second 230 electrodes, to be biocompatible (e.g., to include salts that are naturally present in human urine, sweat, or other fluids), or according to some other considerations. For example, the first electrode 210 could include magnesium metal, the second electrode 230 could include woven carbon fiber and/or activated carbon, and the salt could include sodium chloride.

The fluid-sensitive battery 200 could be configured to provide an electrical voltage according to a variety of different chemistries. Such chemistries could be set by the chemical composition of the first 210 and second 230 electrodes and/or the chemical composition of any electrolytes present in the battery 200. For example, the battery 200 could operate according to a magnesium-air chemistry such that, when the battery 220 is exposed to oxygen from the environment of the battery 200, the oxygen reacts with magnesium metal of the first electrode 210 to generate a voltage and/or current between/through the first 210 and second 230 electrodes. In such an example, the second electrode 230 could be a carbon fiber electrode (e.g., the second electrode 230 could include an element of woven carbon fiber impregnated with particles of activated carbon, to increase the effective surface area of the second electrode 230) and an electrolyte that includes sodium chloride could be disposed (as a dry salt) on or within one or both of the separator 220 or the second electrode 230. Operation of such a fluid-sensitive battery to, in the presence of an aqueous solution, provide a voltage could include generating magnesium hydroxide as a result of oxidation of the magnesium metal of the first electrode 210.

A fluid-sensitive battery as described herein could include additional or alternative elements to those described in relation to the example fluid-sensitive battery 200 of FIGS. 2A and 2B. For example, a fluid-sensitive battery could include an encapsulating overlayer configure to protect the battery, to prevent the movement of certain chemicals into or out of the battery (e.g., to prevent irritating chemicals from exiting the battery), or to provide some other functionality. A moisture-detecting device (e.g., 110) could include multiple fluid-sensitive batteries disposed at multiple different locations to detect the presence of moisture at the multiple different locations. A moisture-detecting device could include multiple fluid-sensitive batteries that are configured in respective different ways (e.g., different battery chemistries, overlayers configured to allow the passage of different sets of chemicals) such that the different batteries can be operated to detect the presence or amount of different analytes in a fluid of interest (e.g., to detect the amounts of different ions or other analytes in urine).

A fluid-sensitive battery as described herein could be configured to provide sufficient electrical power or energy to operate a controller, transmitter, or other electronics. For example, an amount and/or area of magnesium metal (or other electrode elements) could be specified to provide an amount of current (e.g., the area of magnesium metal could be greater than 1 square centimeter to provide more than 2 mA of current) and/or a thickness of the magnesium metal could be specified such that the battery provides electrical power for a specified duration.

A moisture-detecting device could additionally or alternatively include other moisture-detecting means. In some examples, a moisture-detecting device could include an element of dissolvable conductive material. Such an element of dissolvable conductive material could be used to detect the presence of moisture by detecting whether and/or to what degree the dissolvable conductive material has dissolved. Such a moisture sensor could be fabricated at low cost by using inkjet printing, screen printing, or other low-cost methods for depositing, on a substrate, precursor materials that could be dried, exposed to ultraviolet radiation, or otherwise cured to form an element of dissolvable conductive material.

Operating such a moisture sensor to detect the presence of moisture could include detecting a resistance of the element of dissolvable conductive material (e.g., by applying a specified current through electrodes or other conductive elements coupled to the element of dissolvable conductive material and detecting a voltage across the element of dissolvable conductive material), using the element of dissolvable conductive material as an element of a resistor network that is connected to a comparator or reset pin of a controller, or using the element of dissolvable conductive material in some other way to detect the presence of moisture proximate to a moisture-detecting device that includes the element of dissolvable conductive material.

Figure 3A:
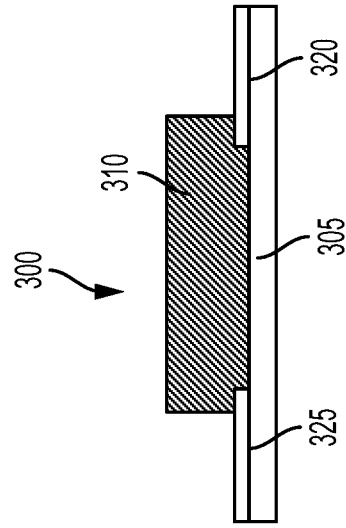
FIG. 3A is a perspective view of a moisture sensor.
Figure 3B:
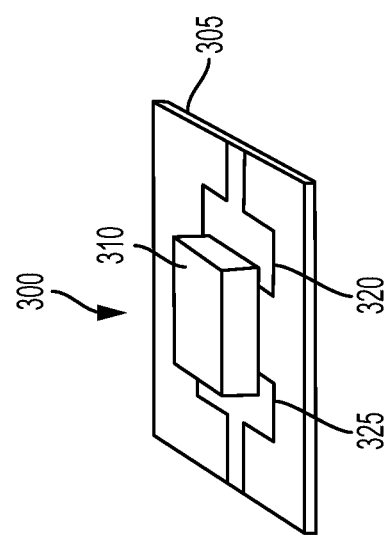
FIG. 3B is a cross-sectional view of the moisture sensor of FIG. 3A.

FIGS. 3A and 3B illustrate perspective and cross-sectional views, respectively, of an example moisture sensor 300 disposed on a substrate 305. The moisture sensor 300 includes a dissolvable conductive material 310 that is connected between first 320 and second 325 conductive traces. The conductive traces 320, 325 and the dissolvable conductive material 310 are disposed on a substrate 305. The dissolvable conductive material 310 is able to conduct an electrical current between the traces 320, 325 and dissolves when exposed to an aqueous fluid. This is illustrated in FIGS. 3C and 3D.

Figure 3C:
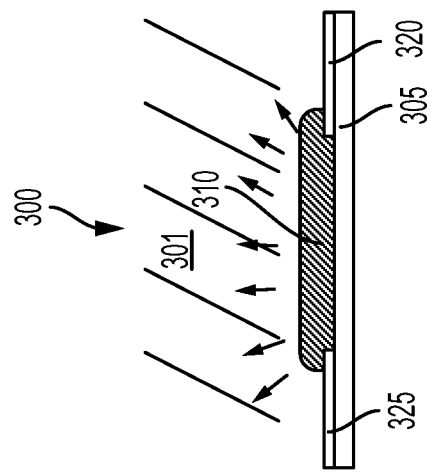
FIG. 3C is a cross-sectional view of the moisture sensor of FIG. 3B after a portion of the moisture sensor has dissolved.
Figure 3D:
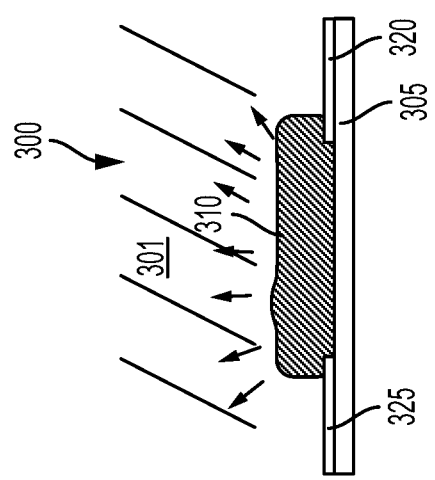
FIG. 3D is a cross-sectional view of the moisture sensor of FIG. 3C after a portion of the moisture sensor has dissolved.

FIG. 3C shows the moisture sensor 300 when it is exposed to an aqueous fluid 301 during a first period of time. An amount of the dissolvable conductive material 310 has dissolved into the aqueous fluid 301. As a result, the resistance of the dissolvable conductive material 310, as measured between the first 320 and second 325 traces, is increased relative to the resistance of the dissolvable conductive material 310 before being exposed to the aqueous fluid 301 (e.g., as illustrated in FIGS. 3A and 3B). FIG. 3D shows the moisture sensor 300 when it is exposed to an aqueous fluid 301 during a second period of time subsequent to the first period of time. A further amount of the dissolvable conductive material 310 has dissolved into the aqueous fluid 301 relative to the first period of time. As a result, the resistance of the dissolvable conductive material 310 is increased relative to the resistance of the dissolvable conductive material 310 during the first period of time (e.g., as illustrated in FIG. 3C).

The dissolvable conductive material 310 could be composed of any material or combination of materials such that the dissolvable conductive material 310 conducts electricity and further such that the dissolvable conductive material 310 can dissolve in an aqueous fluid. The dissolvable conductive material 310 could be composed of a substance that is both intrinsically conductive and soluble in water, for example, a soluble conductive polymer that includes poly(3,4-ethylenedioxythiophene) (also known as PEDOT).

Additionally or alternatively, the dissolvable conductive material 310 could include a plurality of conductive elements (e.g., metal fibers, wires or particles) disposed within a medium that dissolves in an aqueous fluid. Such a dissolvable conductive material 310 could be configured such that, when the medium dissolves into the aqueous solution, the dissolvable conductive material 310 increases in resistance due to loss or disconnection of the plurality of conductive elements and/or due to some other process. For example, the plurality of conductive elements could include fibers or microparticles composed of silver, carbon, or of some other conductive material. The medium that dissolves in an aqueous fluid could include polyvinyl alcohol (PVA), PEDOT, or some other dissolvable material. The dissolvable conductive material 310 could include additives or otherwise be configured to control a rate of dissolution of the material into an aqueous solution, e.g., by controlling an amount of crosslinking and/or a length of polymers comprising the dissolvable conductive material 310.

A moisture sensor that includes a dissolvable conductive material could include additional or alternative elements to those illustrated in FIGS. 3A-D. For example, a moisture sensor could include an overlayer formed over an element of dissolvable conductive material to control a rate at which the dissolvable conductive material dissolves when exposed to an aqueous solution. Such an overlayer could be provided to decrease the rate at which the dissolvable conductive material dissolves in order to increase a sensitivity of the moisture sensor to an amount, an osmolarity, or some other property of an aqueous fluid to which the dissolvable conductive material is exposed. Additionally or alternatively, such an overlayer could be provided to delay the dissolution of the dissolvable conductive material and/or to prevent incidental moisture (e.g., condensation from the atmosphere) from causing the dissolvable conductive material to dissolve.

In some examples, an overlayer disposed on a dissolvable conductive material of a moisture sensor could include a material that dissolves in an aqueous fluid. Such a dissolvable overlayer could be provided to act as an ablative layer, delaying the dissolution of the dissolvable conductive material when the dissolvable conductive material and overlayer are exposed to the aqueous fluid. Such an overlayer could be composed of polyvinyl alcohol or some other water-soluble material.

FIGS. 4A-C illustrate a moisture sensor 400 that includes such an overlayer. The moisture sensor 400, as illustrated in FIG. 4A before the sensor is exposed to an aqueous fluid, includes a dissolvable conductive material 410 over which is disposed an overlayer 430 that includes a material that dissolves in the aqueous fluid. The dissolvable conductive material 410 is disposed on a substrate 405 and is in contact with conductive traces 420, 425.

FIG. 4B shows the moisture sensor 400 when it is exposed to an aqueous fluid 401 during a first period of time. An amount of the overlayer 430 has dissolved into the aqueous fluid 401. The presence of the overlayer 430 has delayed the dissolution of the dissolvable conductive material 410. As a result, the resistance of the dissolvable conductive material 410, as measured between the traces 420, 425, may be substantially the same as the resistance of the dissolvable conductive material 410 before being exposed to the aqueous fluid 401 (e.g., as illustrated in FIG. 4A). FIG. 4C shows the moisture sensor 400 when it is exposed to the aqueous fluid 401 during a second period of time subsequent to the first period of time. The overlayer 430 has fully dissolved and an amount of the dissolvable conductive material 410 has dissolved into the aqueous fluid 401. As a result, the resistance of the dissolvable conductive material 410 is increased relative to the resistance of the dissolvable conductive material 410 during the first period of time (e.g., as illustrated in FIG. 4B).

In some examples, an overlayer disposed on a dissolvable conductive material of a moisture sensor could include a material that has a specified permeability for an aqueous fluid and/or for one or more constituents of the dissolvable conductive material. Such a specified-permeability overlayer could be provided to control the rate of dissolution of the dissolvable conductive material when the dissolvable conductive material and overlayer are exposed to the aqueous fluid. Such a specified-permeability could have a pore size, a degree of crosslinking, a degree of hydrophilicity, or some other properties specified to control the degree of permeability of the overlayer for the aqueous fluid and/or for one or more constituents of the dissolvable conductive material.

FIGS. 5A and 5B illustrate a moisture sensor 500 that includes such an overlayer. The moisture sensor 500, as illustrated in FIG. 5A before the sensor is exposed to an aqueous fluid, includes first 510a and second 510b dissolvable conductive materials. An overlayer 530b that includes a material that has a specified permeability for an aqueous fluid is disposed on the second dissolvable conductive material 510b. The dissolvable conductive materials 510a, 510b are disposed on a substrate 505. FIG. 5B shows the moisture sensor 500 when it is exposed to an aqueous fluid 501 during a first period of time. An amount of the first dissolvable conductive material 510a has dissolved into the aqueous fluid 501. The presence of the overlayer 530b has resulted in a lesser amount of the second dissolvable conductive material 510b having dissolved into the aqueous fluid 501.

III. Example Electronics of a Moisture Detecting Platform

Figure 6:
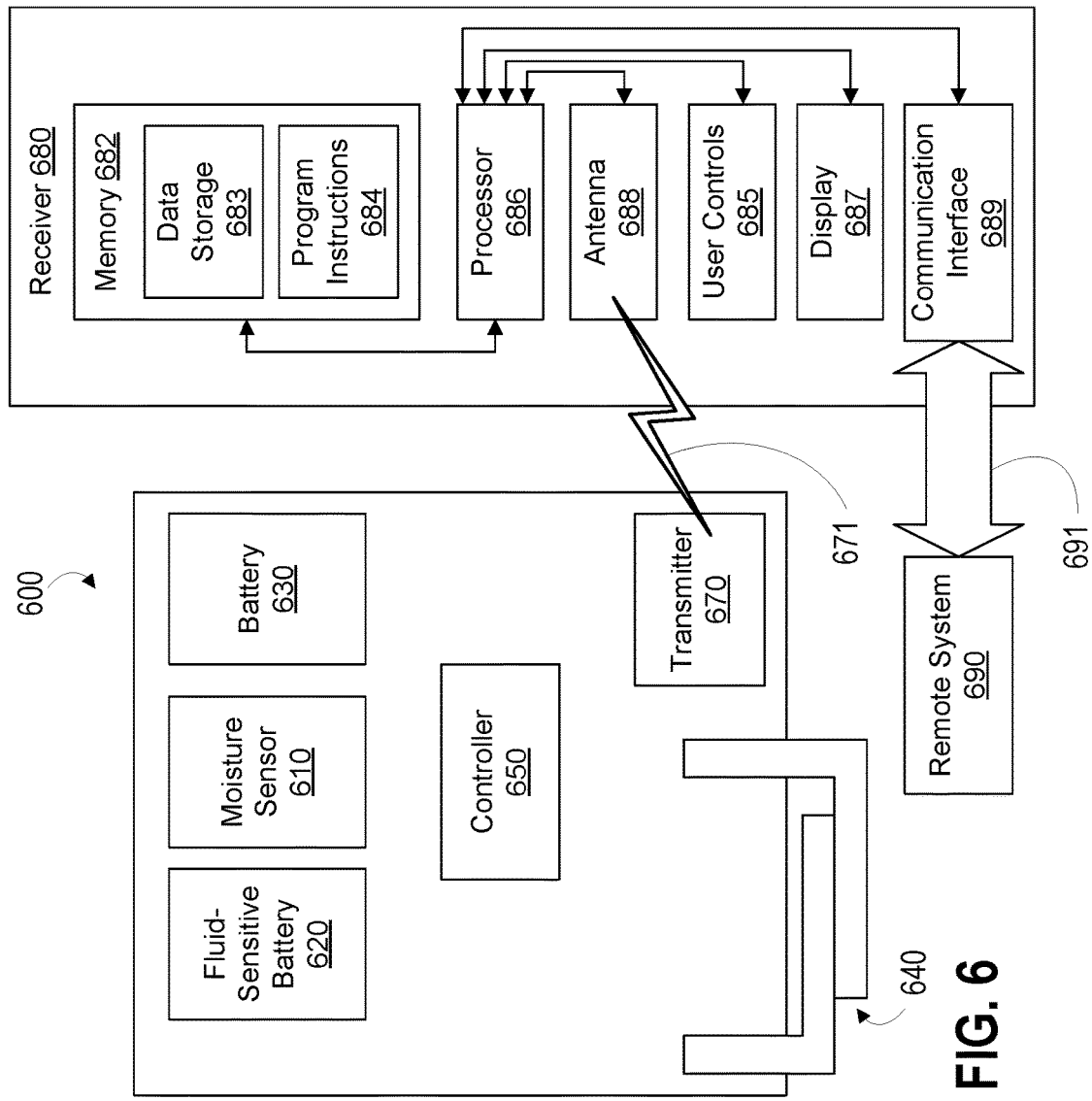
FIG. 6 is a block diagram of an example moisture-sensitive system in wireless communication with an external device.

FIG. 6 is a block diagram of a system that includes a moisture-detecting device 600 configured to transmit radio-frequency signals 671 to a receiver 680. The moisture-detecting device 600 includes a fluid-sensitive battery 620, a moisture sensor 610, a controller 650, a battery 630, conductive clasps 640, and a transmitter 670. The battery 630 supplies operating voltages to the controller 650, moisture sensor 610, transmitter 670, and/or other elements of the moisture-detecting device 600. The device may additionally receive operating voltages from the fluid-sensitive battery 620 when the fluid-sensitive battery 620 is exposed to an aqueous fluid. The moisture sensor 610 includes a dissolvable conductive material and can be operated to determine whether an aqueous fluid is proximate the device 600, e.g., by measuring a resistance of an element of the dissolvable conductive material. The moisture-detecting device 600 could be incorporated into and/or configured as a diaper such that the presence of urine, feces, or other fluids in the diaper could be detected by the device and indicated, via radio-frequency signals, to a smartphone, hospital server, or other receiver device(s) (e.g., 680).

The transmitter 670 is operated by the controller 650 to provide radio frequency transmissions or other wireless signals that may be received by another device, e.g., by the receiver device 680. Such transmissions or other indications could indicate that moisture has been detected (e.g., could include a repeated beacon signal) and/or could provide some additional information (e.g., some detected information about the amount or composition of a detected moisture, a temperature of a body to which the device 600 is mounted).

A moisture-detecting device as described herein could include elements additional to those shown in FIG. 6, could include multiple instances of one or more of the elements illustrated in FIG. 6, could lack one or more of the elements illustrated in FIG. 6, or could have a configuration that otherwise differs from the device 600 illustrated in FIG. 6. For example, the device 600 could lack the battery 630 and moisture sensor 610 and could be powered by the fluid-sensitive battery 620 when the device 600 is exposed to urine or some other aqueous fluid and/or moisture. In another example, the device 600 could lack the fluid-sensitive battery 620 and could be powered by the battery 630 to operate the moisture sensor 610 to detect the presence of moisture proximate the device 600.

The transmitter 670, the fluid-sensitive battery 620, the controller 650, the battery 630, the moisture sensor 610, and other elements of the device 600 can be situated on a flexible substrate. Such a flexible substrate could be sewn into or otherwise adhered on or within a diaper to facilitate detection of urine or other fluids in the diaper. Such a flexible substrate could have a thickness, shape, composition, and/or other properties specified such that the flexible substrate minimally interferes with activities of a wearer of a diaper that includes the device 600. Further, one or more of the components of the moisture-detecting device 600 could be formed on the substrate. For example, conductive traces of circuitry, battery electrodes, sensor electrodes, antennas, or other components of the device 600 could be formed on one or more surfaces of the substrate.

The flexible substrate could be composed of polyimide, polyethylene terephthalate, or some other flexible polymeric or other material. One or more surfaces of the flexible substrate could be used as a platform for mounting components or elements of the transmitter 670, the controller 650, the fluid-sensitive battery 620, the moisture sensor 610, the battery 630, or other elements of the device 600 such as chips (e.g., via flip-chip mounting) and conductive materials (e.g., via deposition techniques) that form electrodes, antenna(e), coils, RF striplines or filters, switches or contacts (e.g., contact pads to which the conductive clasps 640 may be crimped or otherwise electrically coupled), and/or connections. The composition of the flexible substrate could be specified such that metal contacts, traces, and interconnects can be patterned directly on the surface of the flexible substrate (e.g., by sputtering, CVD, or some other deposition process) and/or on a coating or layer formed on one or more surfaces of the flexible substrate.

The controller 650, transmitter 670, fluid-sensitive battery 620, moisture sensor 610, or other element(s) of the device 600 could include a variety of components or elements. For example, the controller 650 could include a computing device (e.g., a processor and a memory that stores instructions that can be executed by the processor), amplifiers, comparators, logic gates, analog-to-digital converters (ADCs), transmitters (e.g., could include the transmitter 670 or elements thereof), radios, transceivers, or some other component or components. Such components can be mounted to and/or electrically connected via interconnects or traces patterned on a substrate. In some examples, the controller 650 could include a comparator, logic gate, amplifier, electronic switch, or other elements configured to receive an input from the fluid-sensitive battery 620 and/or the moisture sensor 610 and, based on the received input(s), operate the transmitter 670 to transmit a radio-frequency signal in response to the fluid-sensitive battery 620 and/or the moisture sensor 610 being exposed to moisture (e.g., to urine or some other aqueous fluid).

Electrical interconnects (e.g., traces on which a dissolvable conductive material may be disposed), antennas, and/or conductive electrodes (e.g., for a fluid sensitive battery or other type of battery, etc.) can be formed from conductive materials patterned on a substrate or other element(s) of the device 600 by a process for precisely patterning such materials, such as deposition, lithography, etc. Such patterned conductive materials can be, for example, gold, platinum, palladium, titanium, carbon, aluminum, copper, magnesium, silver, silver-chloride, conductors formed from noble materials, metals, combinations of these, etc. Additionally or alternatively, a conductive material (e.g., magnesium) could be deposited on a conductive trace or other formed conductive material via electroplating, chemical vapor deposition, or some other methods.

Further, polymeric or other materials (e.g., dissolvable conductive materials) may be formed on a substrate of the device by a process including chemical vapor deposition, inkjet printing, screen printing, or some other means for depositing material. Such a process could then include a curing process to dry, polymerize, cross-link, or otherwise change a deposited material into an element of the device 600 (e.g., into an element of a dissolvable conductive material). Further, formed elements or components of the device 600 may be subjected to post-formation processes, e.g., to deposit an electrolyte into or on one or more components of a battery. For example, a saline solution could be applied to an absorbent separator, electrode, or other components of a fluid-sensitive battery, and the fluid-sensitive battery could then be dried such that a salt or other components of the saline solution are disposed, in a dry state, on or within the fluid-sensitive battery.

Some elements of the device 600 may be deposited on or within or formed from a diaper. For example, the conductive clasps 640 may comprise a woven or otherwise formed flexible conductive material (e.g., woven strands or wires composed of metal or conductive polymer, a metal foil, a sheet of conductive polymeric material) sewn into a fabric or other material of a diaper. Such clasps could further include a conductive adhesive or other means for connecting the clasps 630 together in a way that provides a mechanical and electrical connection between the clasps 630. The clasps 630 could additionally be electrically coupled to the controller 650 and/or a battery (e.g., 620, 630) of the device. This could include crimping the clasps 630 to conductive areas of the device 600, using a conductive adhesive to affix the clasps 630 to the device 600, connecting the clasps 630 with other elements of the device 600 via conductive thread or wires, or electrically coupling the clasps 630 to the controller 650 or other elements of the device 600 via some other means.

The conductive clasps 640 could be connected to elements of the device 600 (e.g., the controller 650, a battery 620, 630) such that connection and/or disconnection of the clasps 640 can cause a change in the operation of the device 600. For example, the controller 650 could apply a voltage to the clasps 630 or otherwise operate to actively detect whether the clasps 630 are connected to each other and responsively engage in some operations (e.g., to cease generating radio-frequency transmissions using the transmitter 670). Additionally or alternatively, the controller 650 or other elements of the device 600 (e.g., the transmitter 670) could be coupled to a battery (e.g., 620 or 630) via the conductive clasps 640 such that the device 600 begins operating (e.g., to operate the moisture sensor 610 to detect moisture and/or to operate the transmitter 670 to generate radio-frequency transmissions) when the conductive clasps 630 are connected and/or ceases operating when the conductive clasps 630 are disconnected.

One or both of the batteries 620, 630 can be configured to provide energy to power the controller 650, transmitter 670, and/or other elements of the device 600. The batteries 620, 630 could be flexible. For examples, the battery 630 could be a flexible lithium-ion battery, magnesium-air battery, or some other type of flexible battery. In another example, the fluid-sensitive battery 620 could be composed of flexible layers of magnesium metal, a separator material such as paper, and woven carbon fiber. Additionally or alternatively, the battery 630 could be a coin-cell battery or other type of rigid battery. One or both of the fluid-sensitive battery 620 or battery 630 could be formed and subsequently disposed on a substrate or other element of the device 600 (e.g., via an adhesive). Additionally or alternatively, one or more components of the batteries 620, 630 (e.g., one or more electrodes, a layer of electrolyte) could be formed on substrate or other element(s) of the device 600. In an example, elements of one or both of the batteries 620, 630 could be printed or otherwise formed on a substrate of the device 600, e.g., by inkjet or screen printing of an electrolyte material on an electrode.

The controller 650 may include a variety of components operably coupled to the transmitter 670 and fluid-sensitive battery 620 and/or moisture sensor 610 or other elements of the device 600 such that the controller 650 can operate the transmitter 670 to generate radio-frequency signals (e.g., Bluetooth Low Energy packets) in response to the device 600 being exposed to an aqueous fluid or some other moisture. The controller 650 could include a computing device, e.g., a device that includes a processor and a memory. The controller 650 may include an ADC configured to receive an electrical signal that is generated by the fluid-sensitive battery 620, moisture sensor 610, and/or other components of the device 600 (e.g., an amplifier or buffer configured to condition the output of the moisture sensor 610) and that is related to the presence of an aqueous fluid and/or other moisture proximate the device 600. The ADC could generate a digital code based on the received electrical signal and the generated code could be recorded, transmitted, visually indicated, used to detect a trigger event, used in combination with other generated codes to determine the presence, amount, or other properties of an aqueous fluid and/or moisture to which the device 600 is exposed.

Additionally or alternatively, the controller 650 may include one or more comparators, electronic switches, logic gates, or other components that are configured to receive an electrical signal that is generated by the fluid-sensitive battery 620 and/or moisture sensor 610 and to output, based on the received signal, a digital signal to control the transmitter 670 and/or other elements of the device 600.

A comparator of the controller 650 could generate a digital high signal when a received moisture-related signal is above or below a specified threshold. For example, the moisture-related signal could be related to a resistance of the moisture sensor 610. Such a signal could be generated by connecting the moisture sensor 610 and a resistor together to form a voltage divider circuit that is connected to one or both of the batteries 620, 630. A voltage output of such a voltage divider circuit could be related to the resistance of the moisture sensor 610, which could, in turn, be related to an amount of a dissolvable conductive material of the moisture sensor 610 that has been dissolved into an aqueous fluid or other moisture to which the device 600 is exposed. When the voltage output is below a specified voltage threshold that corresponds to the resistance of the moisture sensor 610 being below a threshold resistance, the comparator could output a signal that could be used, e.g., to maintain the controller 650 in a reset state (e.g., a low-power mode) or otherwise prevent the transmitter 670 from generating radio-frequency signals. Additionally or alternatively, when a voltage signal corresponding to the resistance of the moisture sensor 610 being above a threshold resistance, a signal could be generated to cause the transmitter 670 to generate radio-frequency signals.

The controller 650 may include a computing device comprising a memory that can be used to store information, e.g., to record voltage measurements related to the presence of an aqueous fluid or other moisture proximate the device 600 (e.g., voltages provided by the fluid-sensitive battery 620, voltages related to the resistance of the moisture sensor 610) and/or to store program instructions that could be executed by a processor of the controller 650 to provide operations of the moisture-detecting device 600.

The transmitter 670 and/or the controller 650 can optionally include one or more oscillators, mixers, frequency injectors, etc. to generate radio-frequency transmissions. Such components could be configured to modulate and/or demodulate information on a carrier frequency to be transmitted by an antenna (e.g., a fractal antenna, a stripline antenna, a dipole antenna, a ceramic chip antenna, a helical antenna) of the transmitter 670. The wireless transmissions so generated by the transmitter 670 are radiative radio-frequency wireless transmissions; in particular, the generated transmissions can propagate, as electromagnetic waves, from the moisture-detecting device 600 (e.g., from an antenna of the device 600) through space to another system (e.g., the illustrated receiver 680) that is located some distance from the moisture-detecting device 600 (e.g., more than a meter away from the device 600).

In response to detecting the presence of moisture proximate the device 600 (e.g., using the fluid-sensitive battery 620 and/or the moisture sensor 610), the transmitter 670 could be operated to generate radio-frequency signals. Such signals could provide an indication, to a smartphone or to some other external system, that moisture has been detected by the moisture-detecting device 600 and/or could indicate some other information (e.g., a detected temperature, amount of the detected moisture, a concentration of an ion or other analyte in the detected moisture). The wireless signals could be transmitted according to one or more wireless signaling standards, e.g., according to the Bluetooth (e.g., Bluetooth Low Energy), ZigBee, WiFi, LTE, and/or some other wireless communications standard or scheme. In some examples, such communications (e.g., data transmitted from the device 600) could be cryptographically secured; that is, the wireless communications link could be encrypted. To save power, the transmitter 670 could act to transmit radio-frequency signals (e.g., information packets) without receiving any wireless transmissions from external systems that may receive such transmissions (e.g., without receiving acknowledgment signals, checksums, or other wirelessly transmitted information indicative of the success of an external system in receiving the transmissions). For example, the transmitter 670 could function as a Bluetooth Low Energy beacon to transmit identification information about the moisture-detecting device 600, an alert indication, or some other information according to the Bluetooth Low Energy (BLE) standard.

As noted above, the control 650 or other elements (e.g., the transmitter 670) of the moisture-detecting device may operate in a low-power mode in order to increase an operational lifetime of the device 600 (e.g., to increase a period of time over which the device 600 may detect moisture and/or provide radio frequency signals related to such detection). Operating in a low-power mode could include removing power from or otherwise deactivating all or portions of the circuitry of the controller 650, e.g., by stopping a clock or oscillator of the controller 650, by disconnecting a clock of the controller 650 from one or more portions of the controller 650, by electrically disconnecting one or more portions of the controller 650 from a battery (e.g., 620, 630), and/or by electrically disconnecting the controller 650 from a battery (e.g., 620, 630). Such operation could include applying a specified voltage (e.g., a logical 'high' voltage or a logical 'low' voltage) to a reset pin or other element(s) of the controller 650. In some examples, this could include receiving a voltage signal that is related to a resistance of the moisture sensor 610 (e.g., a voltage signal from a voltage divider that includes the moisture sensor 610) and maintaining the controller 650 in a low-power mode when the resistance of the moisture sensor 610 is less than a threshold resistance. In another example, this could include receiving a voltage signal from the fluid-sensitive battery 620 and maintaining the controller 650 in a low-power mode until the voltage exceeds a threshold (e.g., until the voltage provided by the fluid-sensitive battery 620 exceeds a threshold that corresponds to the fluid-sensitive battery 620 having been exposed to an aqueous fluid).

It is noted that the block diagram shown in FIG. 6 is described in connection with functional modules for convenience in description. However, embodiments of the moisture-detecting device 600 can be arranged with one or more of the functional modules ("sub-systems") implemented in a single chip, integrated circuit, and/or physical feature or on multiple such elements. Further, a moisture-detecting device as described herein could lack one or more of the illustrated elements, or could include alternatively configured elements. For example, a moisture-detecting device could include only one of a fluid-sensitive battery or a moisture sensor.

The receiver 680 could include or be part of a cellphone, a personal computer, a tablet computer, a hospital information network or alert system, a home automation system, a server or other system in a childcare facility, or some other system configured to receive radio-frequency signals from the moisture-detecting device 600. The receiver 680 includes an antenna 688 (or group of more than one antenna) to receive radio-frequency signals 671 from the transmitter 670 of the moisture-detecting device 600. The receiver 680 also includes a computing system with a processor 686 in communication with a memory 682. The receiver 680 can also include one or more of user controls 685, a display 687, and a communication interface 689. The memory 682 is a non-transitory computer-readable medium that can include, without limitation, magnetic disks, optical disks, organic memory, and/or any other volatile (e.g. RAM) or non-volatile (e.g. ROM) storage system readable by the processor 686. The memory 682 can include a data storage 683 to store indications of data, such as periods of time during which the device 600 transmitted radio-frequency signals, program settings, etc. The memory 682 can also include program instructions 684 for execution by the processor 686 to cause the receiver 680 to perform processes specified by the instructions 684. The program instructions 684 can cause the receiver 680 to perform any of the function described herein. The receiver 680 can also include one or more hardware components for operating the antenna 688 to receive the radio-frequency signals 671 from the transmitter 670. For example, oscillators, frequency injectors, encoders, decoders, amplifiers, filters, etc. can receive signals from the antenna 688 according to instructions from the processor 686.

For example, program instructions 684 may cause the receiver 680 to provide a user interface that allows for display of information related to the operation of the moisture-sensing device 600. Such program instructions 684 may cause the receiver 680 to, responsive to receiving a radio-frequency signal transmitted from the moisture-detecting device 600, operate the display 687 or some other user interface elements of the receiver 680 to generate at least one of a visual stimulus, an audio stimulus, or a haptic stimulus. Such a generated stimulus could be perceived by a user and, in response the user could change a diaper containing the moisture-detecting device 600 or could take some other action (e.g., deactivate electronics containing the device 600, shut off a supply of water to plumbing or machinery on or within which the device 600 is disposed).

The receiver 680 may include additional or alternative elements configured to communicate or otherwise interact with the moisture-detecting device 600 in some other way, e.g., to determine an identity (e.g., a serial number) of the device 600 or to exchange cryptographic key(s). For example, the receiver 680 may include a camera, a light source, and/or other components configured to optically determine some information about the moisture-detecting device 600, e.g., to determine an identity, a serial number, an encryption key, or some other information based on text, a bar code, or some other markings present on the device 600 and/or on packaging or other material associated with the device 600 (e.g., markings present on a diaper that includes the device 600, markings on packaging of such a diaper). In another example, the receiver 680 may include an antenna coil or other means for interacting, via near-field wireless signals, with the device 600. Such interactions could include providing a near-field wireless signal to activate the device 600 (e.g., to cause the controller 650 to transition from a low power mode to a high-power mode). Such interactions could additionally or alternatively include communicating information between the moisture-detecting device 600 and the receiver 680, e.g., to transfer identifying information, cryptographic keys, calibration information, program instructions, or some other information. For example, the receiver 680 could transit a cryptographic key to the moisture-detecting device 600 and the device 600 could use the received cryptographic key to encrypt information sent using the transmitter 670. Such a cryptographic key could be static, and stored in a memory of the moisture-detecting device 600 (e.g., a laser-set read-only memory) and/or could be generated by a random number generator of the device 600 or by some other means.

The receiver 680 can also be configured to include a communication interface 689 to communicate signals via a communication medium 691 to and from a remote system 690. For example, the remote system 690 may be a smart phone, tablet computer, laptop computer, or personal computer, and communication interface 689 and communication medium 691 may be a Bluetooth module and wireless Bluetooth communication signals, respectively. In this example, the receiver 680 may be configured to send information about moisture detected by the moisture-detecting device 600 to the smart phone, tablet computer, laptop computer, or personal computer to facilitate generating an alert that could be perceived by a user. In another example, the remote system 690 is a server at a hospital nurse's station, a childcare facility, or a nursing home, the communication interface 689 is a WiFi radio module, and the communication medium 691 is elements of the internet sufficient to enable the transfer of data between the remote server and the WiFi radio module. A nurse, childcare provider, or other individual may, in response to receiving this data, change a diaper or perform some other action. Further, the receiver 680 may be configured to receive signals from a remote server, such as program updates. Communication interface 689 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The receiver 680 can be a smart phone, digital assistant, or other portable computing device with wireless connectivity sufficient to provide the wireless communication link 671. The receiver 680 can also be implemented as an antenna module that can be plugged in to a portable computing device, such as in an example where the communication link 671 operates at carrier frequencies not commonly employed in portable computing devices.

IV. Example Methods

Figure 7:
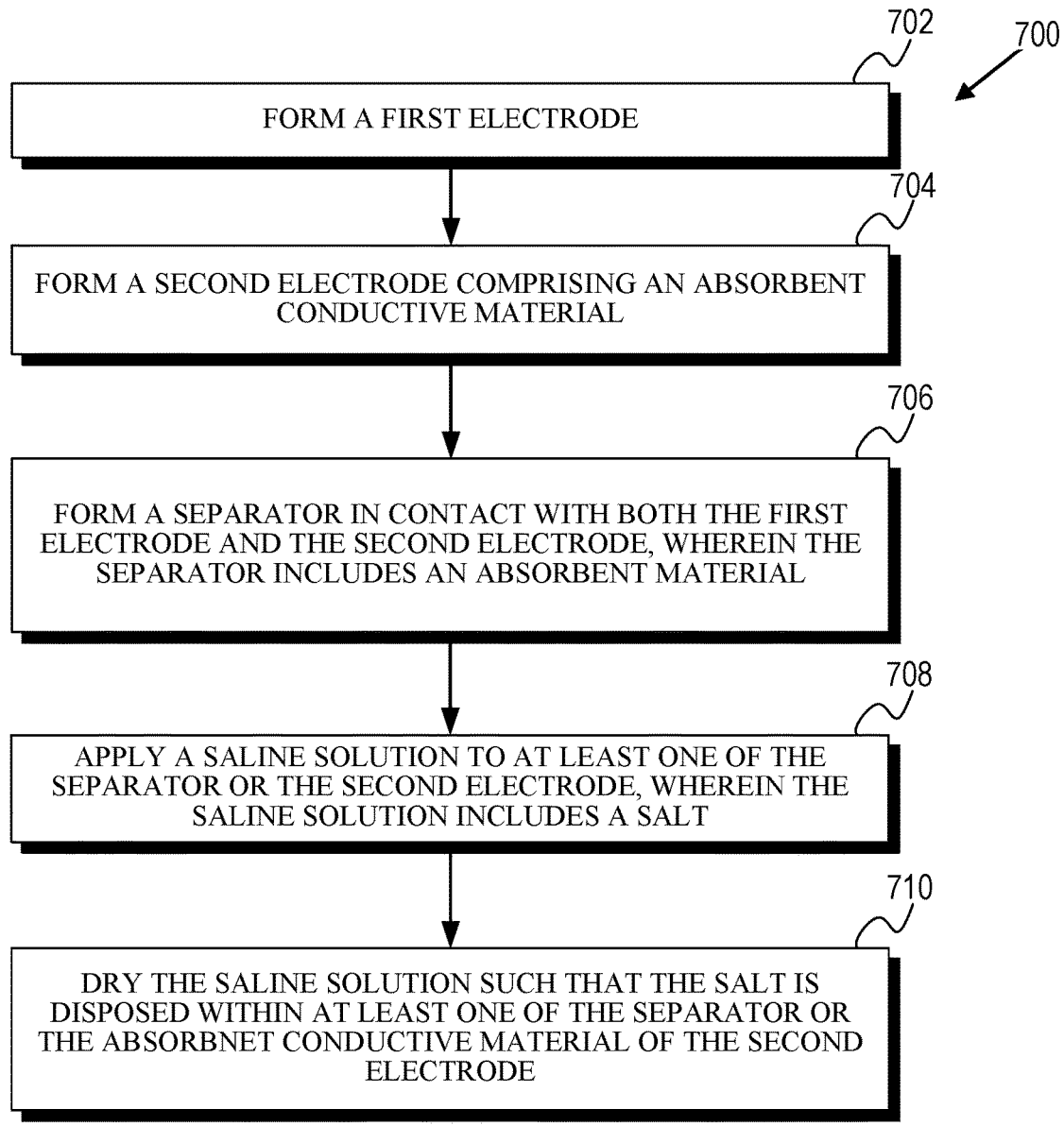
FIG. 7 is a flowchart of an example process.

FIG. 7 is a flowchart of a method 700 for fabricating a fluid-sensitive battery. The method 700 includes forming a first electrode (702). This could include depositing and/or forming a metal or other conductive material of the first electrode on a substrate, e.g., by sputtering, chemical vapor deposition, physical vapor deposition, photopatterning, or some other methods for forming conductive materials on a substrate. Additionally or alternatively, the first electrode could include a foil, wire, mesh, or other formed element and forming the first electrode (702) could include fabricating or assembling such elements and/or disposing such elements on a substrate. The first electrode could include metals (e.g., magnesium, lithium) and/or metal oxides or metal salts (e.g., magnesium oxide, silver chloride). In such examples, forming the first electrode (702) could include forming such metal oxides or salts, e.g., via a process of electroplating, exposure to oxidizing or reducing agents, or some other process.

The method 700 further includes forming a second electrode comprising an absorbent conductive material (704). Such an absorbent conductive material could include a mesh, felt, woven fabric, or other absorbent element composed of fibers or wires of conductive material. For example, the second electrode could include woven carbon fibers. In such examples, forming the second electrode (704) could include weaving such elements to form a fabric. Forming the second electrode (704) could include further processes. For example, the second electrode could include particles of activated carbon fiber disposed within a fabric of woven carbon fibers (e.g., to increase an effective surface area of the second electrode and/or to reduce an effective impedance of the interface between the second electrode and an aqueous solution to which the second electrode is exposed) and forming the second electrode (704) could include a process of impregnating the woven carbon fibers with the particles of activated carbon.

The method 700 yet further includes forming a separator in contact with both the first electrode and the second electrode, wherein the separator includes an absorbent material (706). The separator could include a paper, a woven or felt fabric (e.g., composed of plant, animal, and/or synthetic fibers), an element of expanded polymeric material, or some other absorbent material, and forming the separator (706) could include fabricating such a material. Further, the separator could be formed from and/or coated with a hydrophilic material or coating to enhance the absorption of an aqueous fluid of interest into the separator. Forming a separator in contact with both the first electrode and the second electrode (706) could include forming a sandwich structure with the separator disposed between the first and second electrodes. Forming such a sandwich structure could include applying layers of respective elements on each other (e.g., applying a formed layer of the separator on a formed first electrode and applying a layer of the second electrode onto a layer of the separator) and/or forming one or more of the first electrode, second electrode, and/or separator on one of the other elements. For example, a separator could be formed on an already-formed first electrode by disposing some precursor material (e.g., a solution comprising a monomer, a solution comprising paper fibers and binding substances) on the first electrode and subsequently drying, polymerizing, or otherwise curing the precursor material to form the separator.

The method 700 further includes applying a saline solution to at least one of the separator or the second electrode, wherein the saline solution includes a salt (708). The saline solution could include a variety of salts or other electrolytes according to the chemistry of the fluid-sensitive battery and/or the composition of the first and/or second electrodes. Further, the salt or other contents of the solution could be specified to be biocompatible or according to some other consideration. In an example, the first electrode could include magnesium metal, the second electrode could include woven carbon fiber, and the saline solution could include sodium chloride. The saline solution could include further salts and/or other contents.

The method 700 further includes drying the saline solution such that the salt is disposed within at least one of the separator or the absorbent conductive material of the second electrode (710). This could include applying heat to the saline solution. Additionally or alternatively, this (710) could include exposing the saline solution to an environment having a controlled pressure and/or humidity, e.g., exposing the saline solution to a vacuum or other low-pressure environment to induce boiling and/or sublimation of liquid portions of the saline solution.

Applying the saline solution (708) and/or drying the saline solution (710) could be performed at any point during the fabrication of the fluid-sensitive battery and/or components thereof. For example, the saline solution could be applied to the separator and/or second electrode before the separator is assembled together with the first electrode and second electrode. In an alternative example, the saline solution could be applied to the separator and/or second electrode following assembly of the first electrode, second electrode, and separator such that the separator is in contact with both the first electrode and the second electrode. The method 700 could include additional or alternative steps to those described here.

Figure 8:
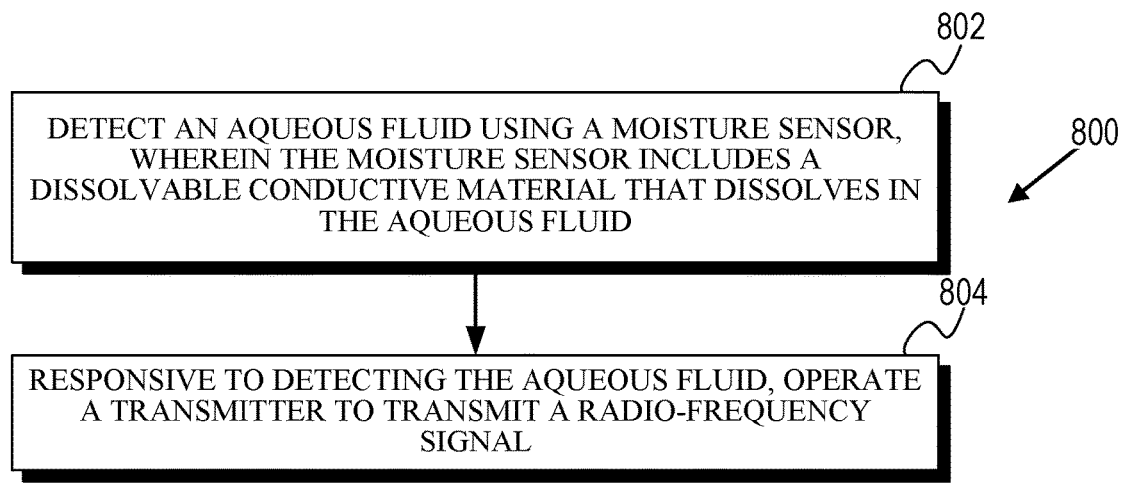
FIG. 8 is a flowchart of an example process.

FIG. 8 is a flowchart of a method 800 for operating a moisture-detecting device. The method 800 includes detecting an aqueous fluid using a moisture sensor, wherein the moisture sensor includes a dissolvable conductive material that dissolves in the aqueous fluid (802). This could include detecting a resistance of an element of dissolvable conductive material, e.g., by applying a specified current through the dissolvable conductive material and detecting a corresponding voltage across the dissolvable conductive material. In another example, the dissolvable conductive material of the moisture sensor could be part of a voltage divider circuit (e.g., by being connected in series with a resistor, with another element of dissolvable conductive material, or with some other electronic element) and a voltage generated by the voltage divider circuit could be detected and used to detect the presence of the aqueous fluid. Detecting an aqueous fluid (802) could include detecting an electrical signal or property of the moisture sensor (e.g., a voltage, a current, a resistance) at one or more points in time and performing some determination based on the detected property. For example, a detected resistance of the moisture sensor could be compared to a threshold resistance to determine whether an aqueous fluid is present. Additionally or alternatively, a voltage or other output of the moisture sensor could be applied to a comparator, a reset pin of a controller, or some other circuit or logic element to generate an output related to the presence of the aqueous fluid.

The method 800 further includes, responsive to detecting the presence of the aqueous fluid, operating a transmitter to transmit a radio-frequency signal (804). This could include transmitting one or more beacon packets or other information according to the Bluetooth Low Energy communications protocol. The radio-frequency signal could be a carrier signal and/or could include some modulation to indicate some information (e.g., information about the amount, contents, or other information about a detected fluid, identification information about a device of which the transmitter is a part).

The method 800 could include additional or alternative elements. For example, the method 800 could include beginning to operate the moisture sensor in response to some input or condition, e.g., in response to conductive clasps of a diaper that includes the transmitter being connected. Additionally or alternatively, the method 800 could include ceasing transmission in response to some input or condition, e.g., in response to such conductive clasps being disconnected. The method 800 could include further elements.

Figure 9:
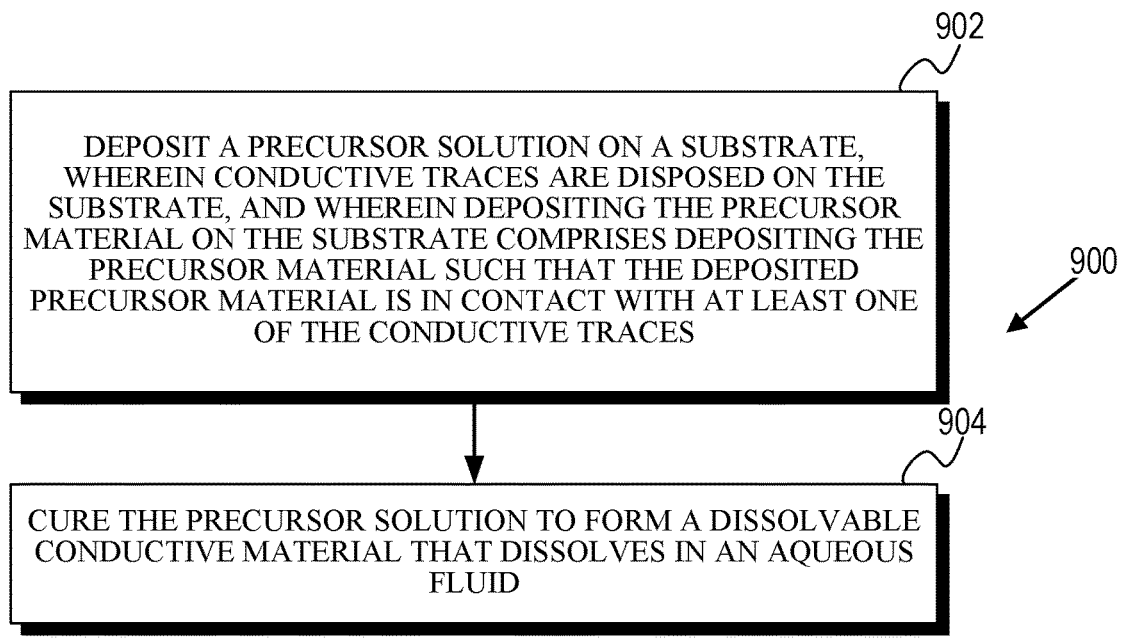
FIG. 9 is a flowchart of an example process.

FIG. 9 is a flowchart of a method 900 for fabricating a moisture sensor. The method 900 includes depositing a precursor solution on a substrate, wherein conductive traces are disposed on the substrate, and wherein depositing the precursor material on the substrate comprises depositing the precursor material such that the deposited precursor material is in contact with at least one of the conductive traces (902). This could include using inkjet printing, screen printing, or some other method to deposit the precursor solution according to a specified pattern relative to the traces on the substrate. The method 900 additionally includes curing the precursor solution to form a dissolvable conductive material that dissolves in an aqueous fluid (904). This could include drying the precursor solution, e.g., to remove a solvent from the solution. Additionally or alternatively, this (904) could include applying ultraviolet radiation, a controlled environment, heat, or some other factor to cause elements of the solution to polymerize. In some examples, curing the precursor solution (904) could include providing a specified period of time during which the precursor solution may polymerize or otherwise form, via internal processes, the dissolvable conductive material (e.g., via activity of a radical polymerization initiator or some other polymerization-initiating substance). The method 900 could include additional or alternative steps to those described here.

Figure 10:
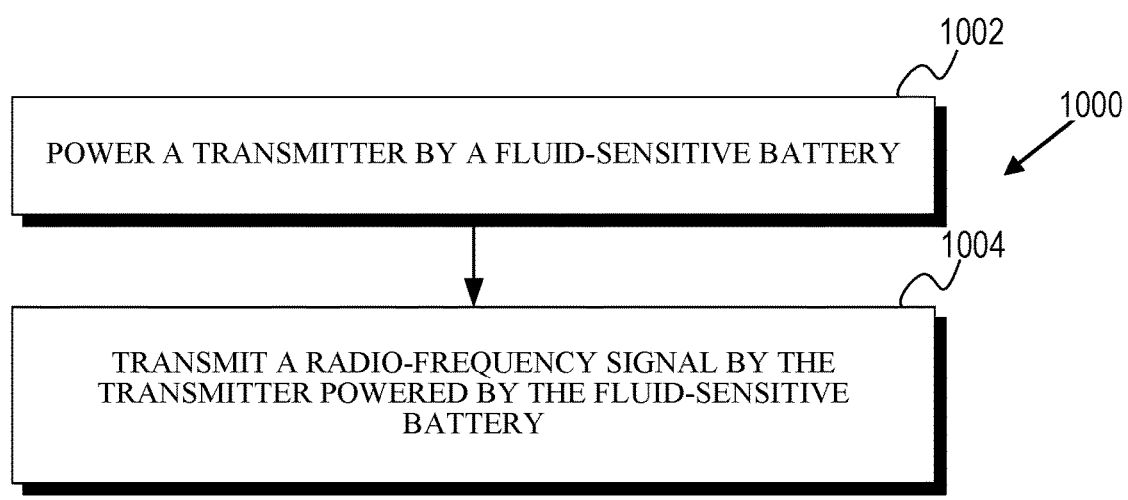
FIG. 10 is a flowchart of an example process.

FIG. 10 is a flowchart of a method 1000 for operating a moisture-detecting device. The method 10 includes powering a transmitter by a fluid-sensitive battery (1002). The fluid-sensitive battery includes a metallic first electrode (e.g., a magnesium metal electrode) and a second electrode composed of an absorbent conductive material (e.g., woven carbon fibers that may be impregnated with particles of activated carbon). The first and second electrodes are separated by an absorbent separator. A salt is disposed, dry, within one or both of the separator and the second electrode. Powering the transmitter (1002) could include coupling the transmitter to the fluid-sensitive battery, e.g., via an electronic switch, by connecting two or more conductive clasps, or via some other means. Powering the transmitter (1002) could include exposing the fluid-sensitive battery to an aqueous fluid (e.g., urine).

The method 1000 further includes transmitting a radio-frequency signal by the transmitter powered by the fluid-sensitive battery (1004). Transmitting the radio-frequency signal (1004) could include the transmitter, responsive to receiving electrical power from the fluid-sensitive battery, generating the radio-frequency signals. Additionally or alternatively, a controller could, based on the voltage provided by the fluid-sensitive battery, operate the transmitter to generate the radio-frequency signals. Such a controller could, itself, be powered by the fluid-sensitive battery. Such a controller could include a computing device (e.g., a processor and/or memory configured to execute stored computer-readable instructions) and/or a comparator, logic gate, or other circuitry configured to operate the transmitter in response to receiving a voltage provided by the fluid-sensitive battery and/or in based on some other inputs. The method 1000 could include additional or alternative elements, e.g., receiving, by a further device, a radio-frequency signals transmitted from the transmitter and, responsive to receiving the RF signal, using a user interface of the further device to generate a visual stimulus, an audio stimulus, a haptic stimulus, or some other stimulus that could be perceived by a person.

This method 1000 could include additional or alternative elements. For example, the method 1000 could include coupling the fluid-sensitive battery to the transmitter and/or other components (e.g., a controller). For example, the transmitter could be coupled to the fluid-sensitive battery via conductive clasps of a diaper that includes the transmitter and fluid-sensitive battery. Additionally or alternatively, the example method could include ceasing transmission in response to some input or condition, e.g., in response to such conductive clasps being disconnected. The method 1000 could include further additional elements.

V. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server. Wireless transmissions of information may be encrypted with a private key or otherwise obfuscated to prevent such transmissions from providing information about the user to unauthorized individuals.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   a transmitter;
   a moisture sensor, wherein the moisture sensor comprises a dissolvable conductive material, wherein the dissolvable conductive material dissolves in an aqueous fluid, wherein the dissolvable conductive material comprises a plurality of conductive elements disposed within a medium that dissolves in the aqueous fluid such that, when the medium dissolves in the aqueous fluid, the plurality of conductive elements become mechanically disconnected from each other; and
   a controller operably coupled to the transmitter and the moisture sensor, wherein the controller:
   operates the moisture sensor to detect the presence of the aqueous fluid proximate the system; and
   operates the transmitter to transmit a radio-frequency signal in response to detecting the presence of the aqueous fluid proximate the system.

2. The system of claim 1, wherein the dissolvable conductive material comprises poly(3,4-ethylenedioxythiophene).

3. The system of claim 1, wherein the plurality of conductive elements comprises conductive silver fibers and wherein the medium that dissolves in the aqueous fluid comprises polyvinyl alcohol.

4. The system of claim 1, wherein the moisture sensor further comprises an over-layer disposed on the dissolvable conductive material, wherein the overlayer comprises a material that dissolves in the aqueous fluid.

5. The system of claim 1, wherein the moisture sensor further comprises an over-layer disposed on the dissolvable conductive material, wherein the overlayer comprises a material that is permeable to the aqueous fluid.

6. The system of claim 1, wherein the controller is coupled to the moisture sensor such that the controller is maintained in a low-power mode when a resistance of the moisture sensor is less than a threshold resistance and wherein the resistance of the moisture sensor is related to an amount of the dissolvable conductive material that has dissolved.

7. The system of claim 1, wherein the moisture sensor is incorporated into a diaper.

8. The system of claim 7, further comprising a battery, wherein the battery, transmitter, and controller are incorporated into the diaper, wherein the diaper comprises first and second conductive clasps that can be connected to each other and disconnected from each other, and wherein the controller is operably coupled to the battery via the first and second conductive clasps.

9. The system of claim 1, wherein operating the transmitter to transmit a radio-frequency signal comprises transmitting one or more radio frequency data packets based on a Bluetooth Low Energy protocol.

10. A method comprising:
    detecting an aqueous fluid using a moisture sensor, wherein the moisture sensor comprises a dissolvable conductive material, wherein the dissolvable conductive material dissolves in the aqueous fluid, wherein the dissolvable conductive material comprises a plurality of conductive elements disposed within a medium that dissolves in the aqueous fluid such that, when the medium dissolves in the aqueous fluid, the plurality of conductive elements become mechanically disconnected from each other; and
    responsive to detecting the aqueous fluid, operating a transmitter to transmit a radio-frequency signal.

11. The method of claim 10, wherein detecting the aqueous fluid using the moisture sensor comprises detecting a resistance of the moisture sensor, wherein the resistance of the moisture is related to an amount of the dissolvable conductive material that has dissolved.

12. The method of claim 10, further comprising:
    receiving, by a further device, the transmitted radio-frequency signal; and
    responsive to receiving the transmitted radio-frequency signal, generating, by a user interface of the further device, at least one of a visual stimulus, an audio stimulus, or a haptic stimulus.

13. The method of claim 10, wherein the moisture sensor is incorporated into a diaper.

14. The method of claim 10, wherein the transmitter is incorporated into the diaper, wherein the diaper comprises first and second conductive clasps that can be connected to each other and disconnected from each other, and wherein the transmitter is operably coupled to a battery via the first and second conductive clasps.

15. The method of claim 14, further comprising connecting the first and second conductive clasps to each other, wherein detecting an aqueous fluid using a moisture sensor is performed responsive to connecting the first and second conductive clasps to each other.

16. The method of claim 10, wherein operating the transmitter to transmit the radio-frequency signal comprises transmitting one or more radio frequency data packets based on a Bluetooth Low Energy protocol.

17. The method of claim 10, wherein the plurality of conductive elements comprises conductive silver fibers.

18. The method of claim 17, wherein the medium that dissolves in the aqueous fluid comprises polyvinyl alcohol.

* * * * *